US00PP32782P2

(12) United States Plant Patent
Bors et al.

(10) Patent No.: US PP32,782 P2
(45) Date of Patent: Feb. 2, 2021

(54) CHERRY TREE NAMED 'BIG RED'

(50) Latin Name: ***Prunus fruiticosa* x *Prunus cerasus***
Varietal Denomination: Big Red

(71) Applicant: Early Morning LLC, Greendale, IN (US)

(72) Inventors: Robert Bors, Saskatoon (CA); Rick Sawatzky, Saskatoon (CA)

( * ) Notice: Subject to any disclaimer, the term of this patent is extended or adjusted under 35 U.S.C. 154(b) by 0 days.

(21) Appl. No.: 16/602,516

(22) Filed: Oct. 22, 2019

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell
(74) *Attorney, Agent, or Firm* — Weatherly IP Solutions, LLC; Barbara Campbell

(57) ABSTRACT

A new and distinct variety of cherry tree having a spreading dwarf bush habit, bright red, elongated, heart-shaped fruit, high flesh to pit ratio, slight sweetness good for eating fresh, and hardy to −40 degrees Celsius, is disclosed.

6 Drawing Sheets

Genus and species: *Prunus fruiticosa* x *Prunus cerasus.*
Denomination: 'Big Red'.

BACKGROUND

'Big Red' is a new and distinct variety of *Prunus fruiticosa* x *Prunus cerasus* cherry tree. 'Big Red' originated from a controlled cross in Saskatoon, Canada in May 1992 between the female parent, 'Egbert Center' (unpatented) and the male parent 'Kelleris 14' (unpatented). Seeds from the cross were planted in March 1993 and a single seedling was selected in 2004. In August 2015, virus-indexed budwood was budded onto 'Carmine Jewel' (unpatented) bush cherry plant in Tipp City, Ohio.

'Big Red' was first asexually propagated in September 2014 in Tipp City, from budding onto 'Carmine Jewel' Rootstock.

Other subsequent asexual propagations were conducted in controlled environments in Tipp City, Ohio and demonstrate that 'Big Red' reproduces true to type in successive generations of asexual reproduction via softwood cuttings.

SUMMARY

The following are the most outstanding and distinguishing characteristics of this new variety when grown under normal horticultural practices in Tipp City, Ohio.

1. Spreading dwarf bush habit;
2. Bright red, elongated, heart-shaped fruit;
3. High flesh to pit ratio;
4. Slight sweetness good for eating fresh; and
5. Hardy to −40 degrees Celsius.

DESCRIPTION OF THE PHOTOGRAPHS

This new Cherry plant is illustrated by the accompanying photographs which show the plant's overall plant habit including form, foliage, bark and flowers. The photographs are of trees grown outdoors in Tipp City, Ohio in May 2019.

The colors shown are as true as can be reasonably obtained by conventional photographic procedures.

DETAILED DESCRIPTION

Figure 1:
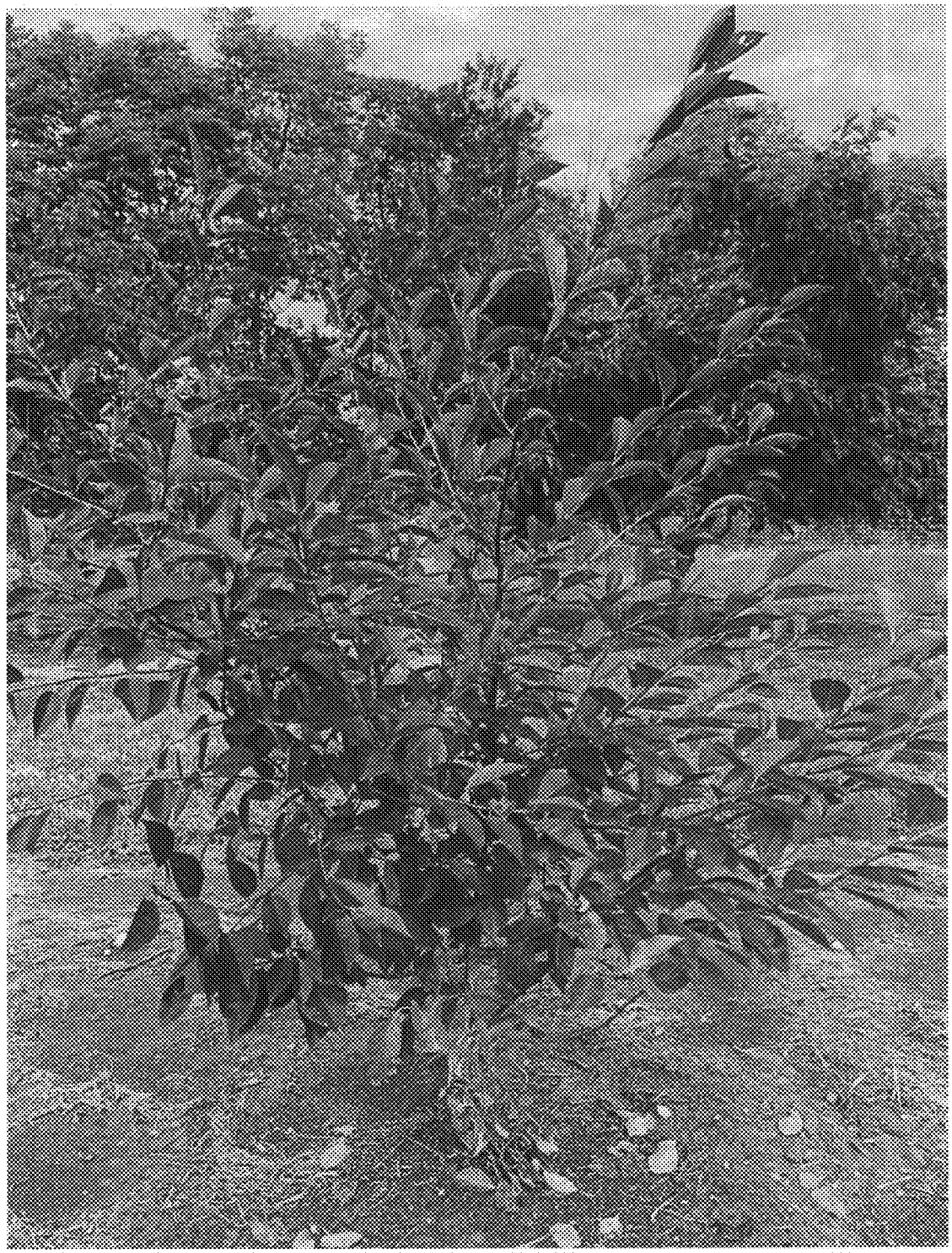
FIG. 1 shows the overall plant habit of a 5-year-old tree of 'Big Red'.
Figure 2:
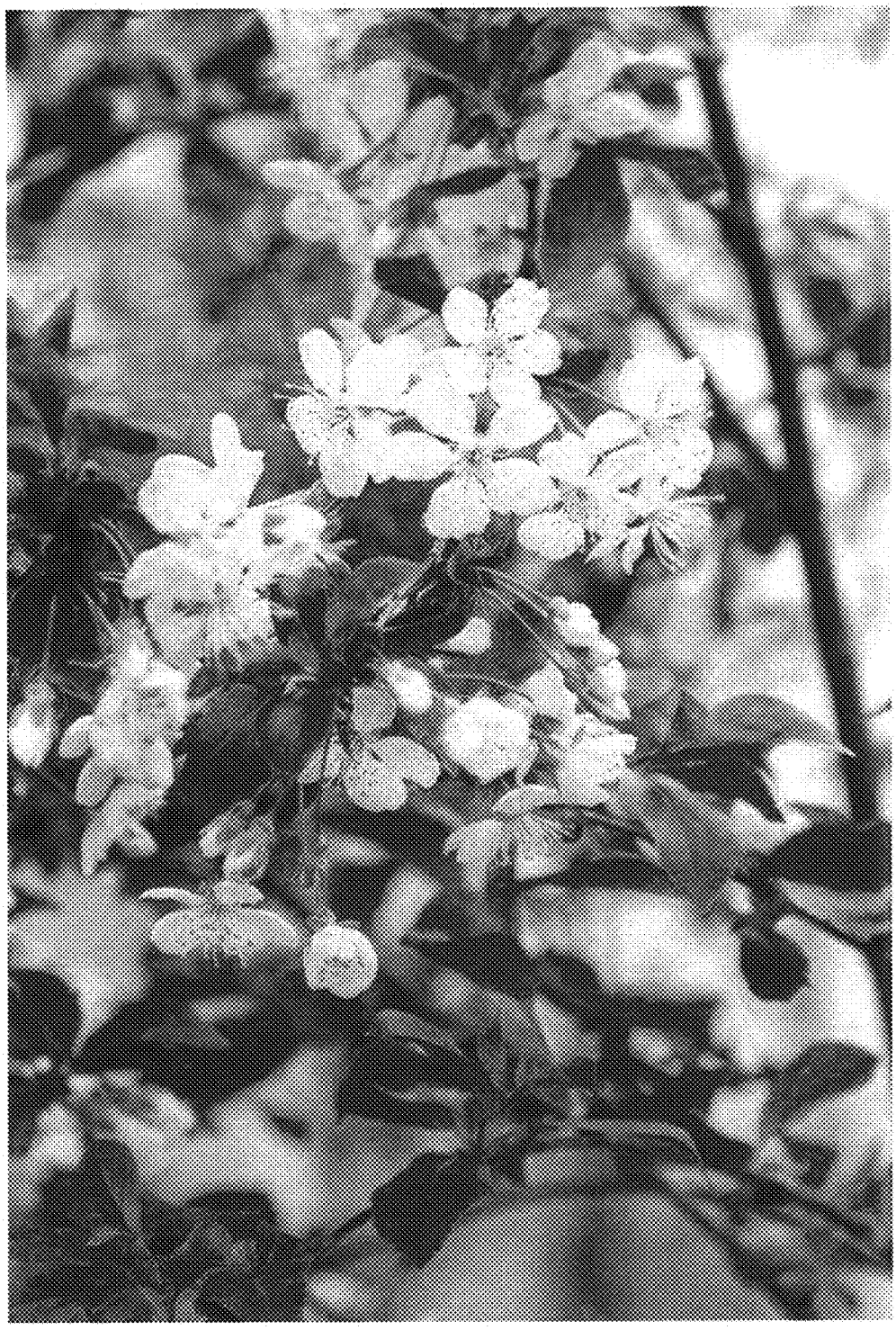
FIG. 2 shows a close-up of the flowers and flower buds of 'Big Red'.
Figure 3:
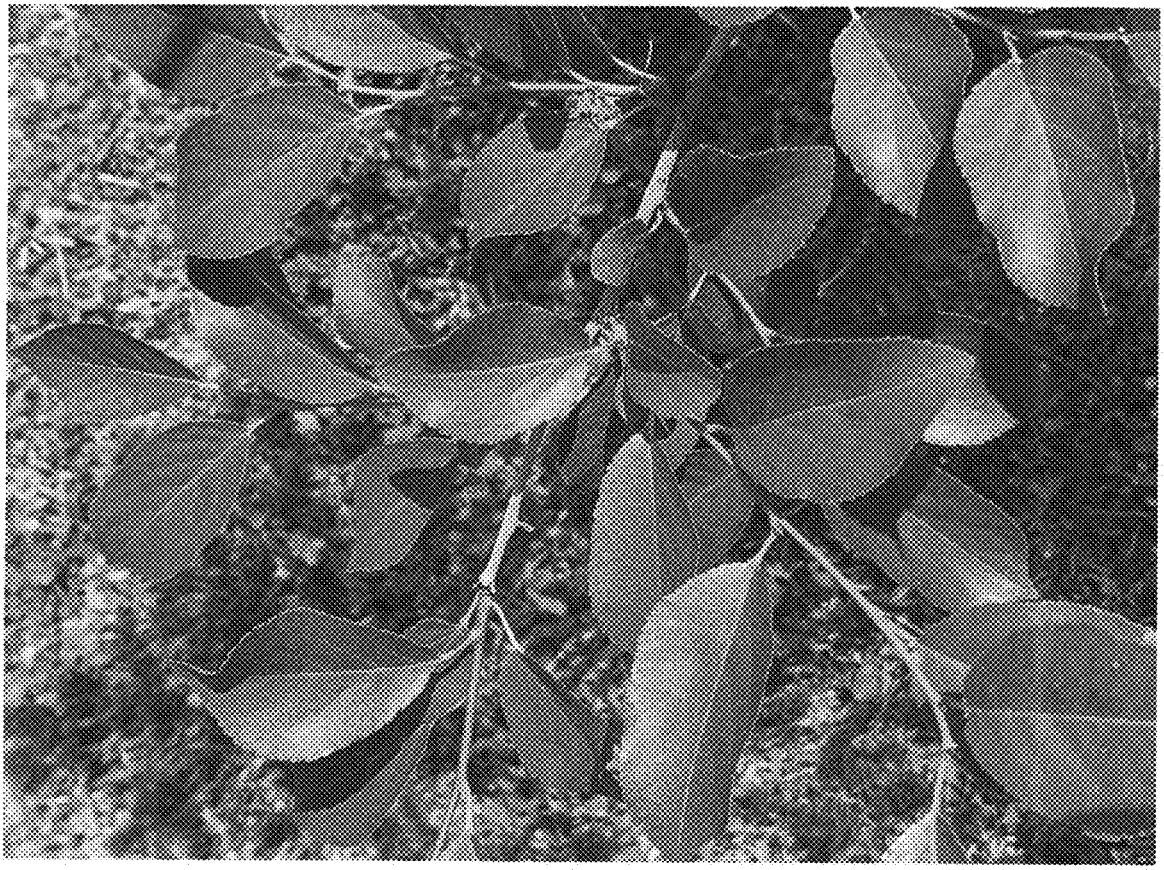
FIG. 3 shows the leaves from a 5-year-old tree of 'Big Red'.
Figure 4:
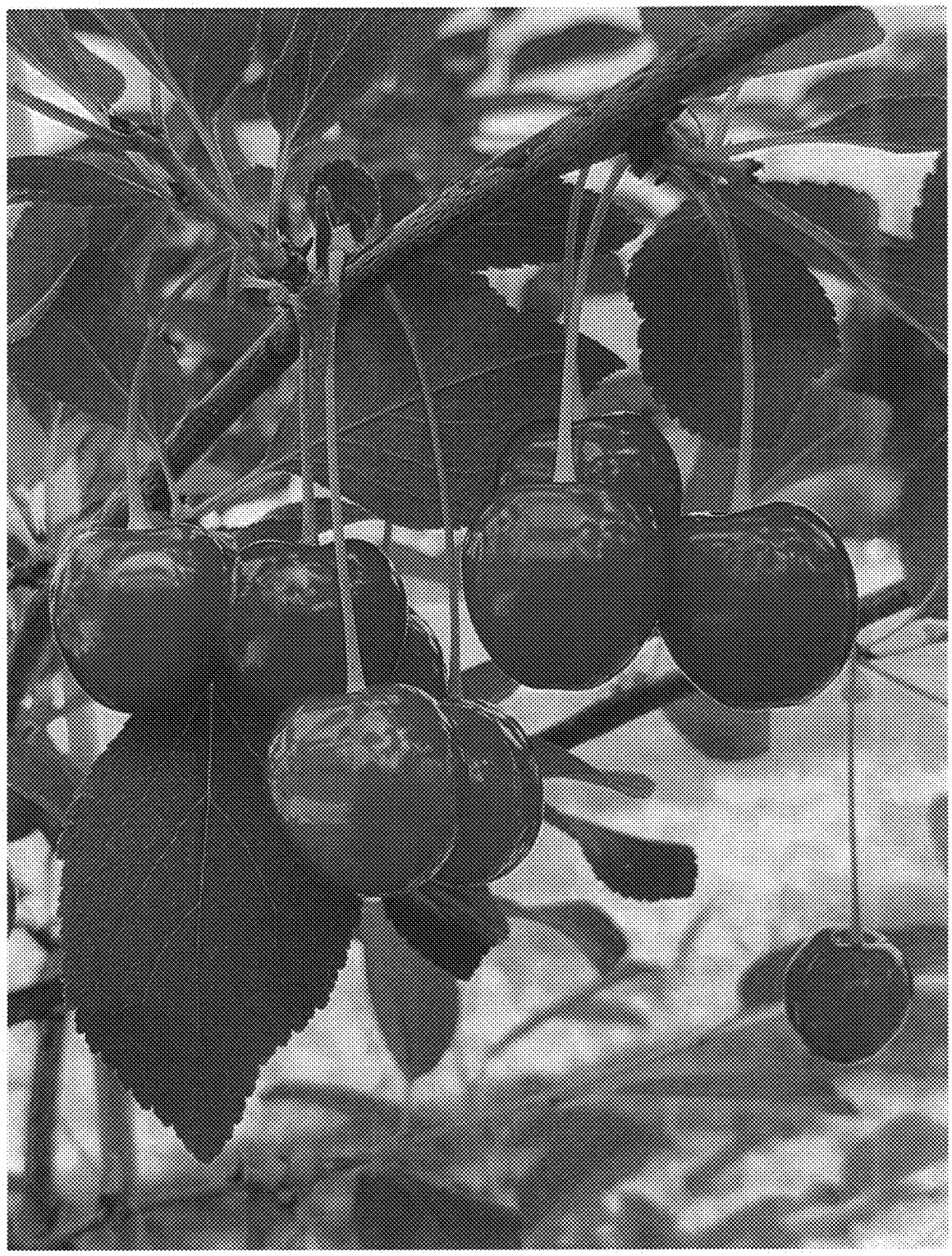
FIG. 4 shows the fruit from a 5-year-old tree of 'Big Red'.
Figure 5:
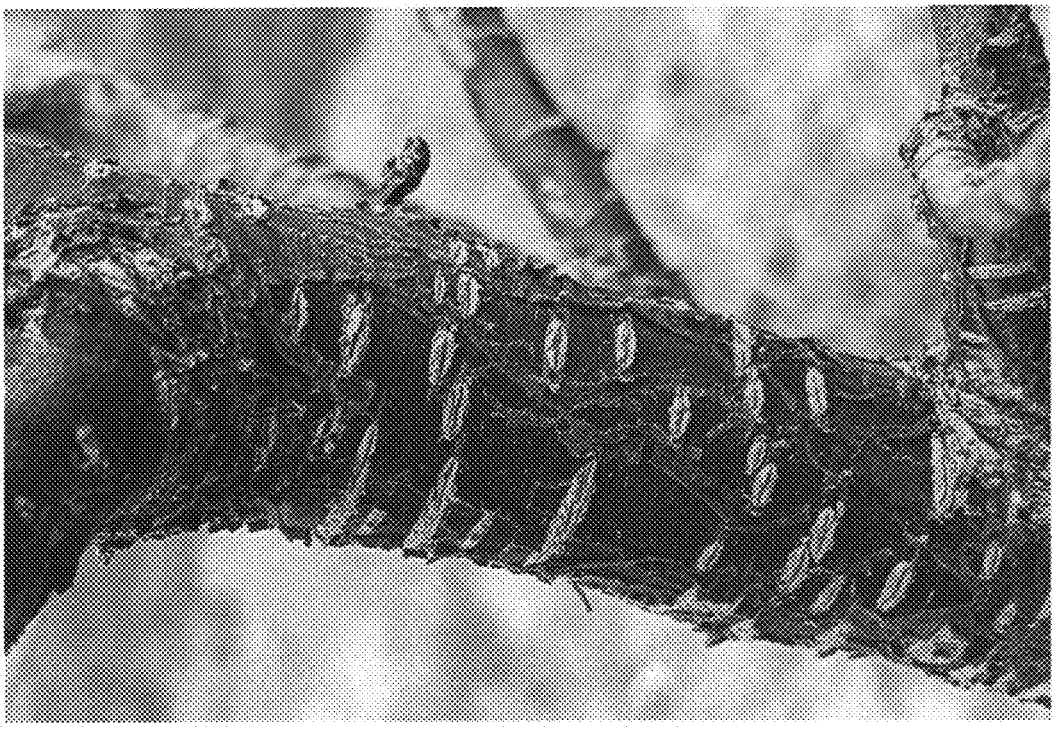
FIG. 5 shows a close-up of the bark of a 3-year-old tree of 'Big Red'.
Figure 6:
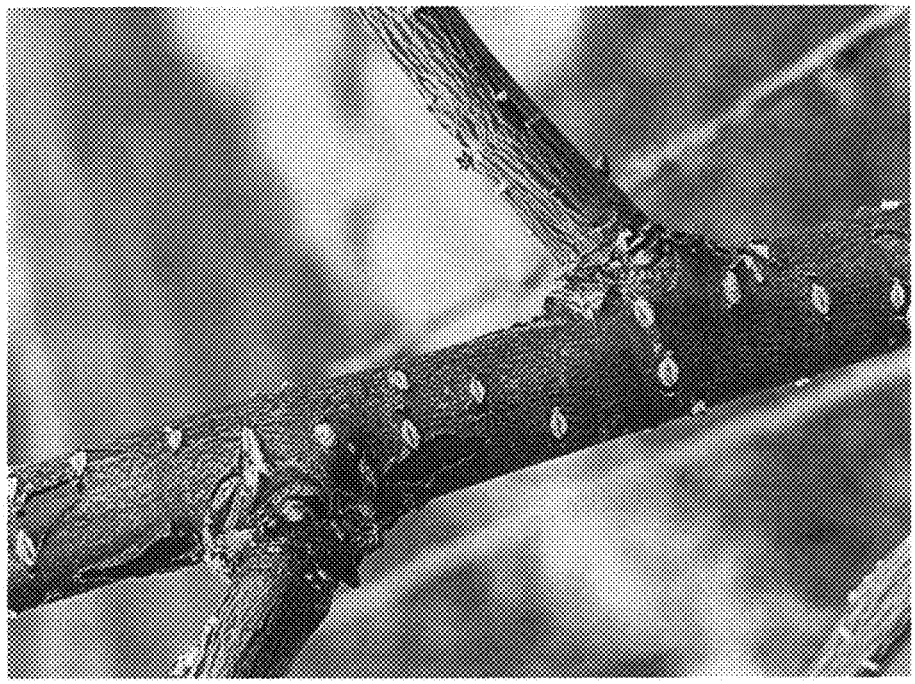
FIG. 6 shows a close-up of the bark of a 2-year-old tree of 'Big Red'.
Figure 7:
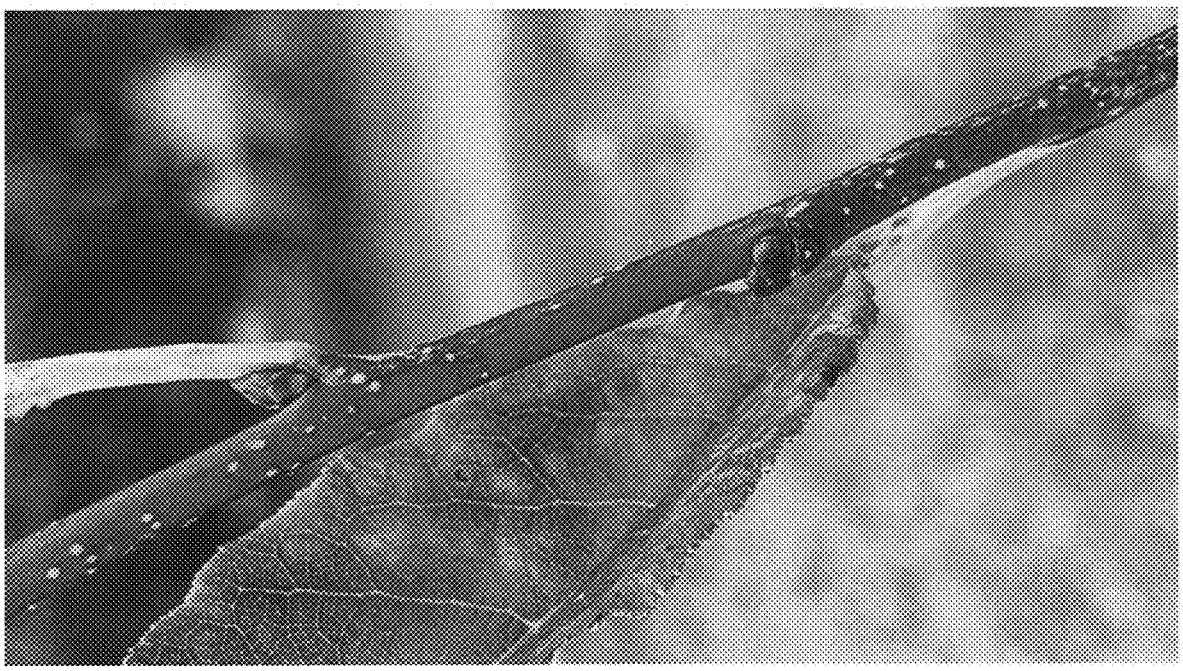
FIG. 7 shows a close-up of the bark of a 1-year-old tree of 'Big Red'.

The following detailed descriptions set for the distinctive characteristics of 'Big Red'. The data which define these characteristics were collected outdoors and in a glasshouse in Tipp City, Ohio. Trees were evaluated from April to July 2019 on 5-year-old trees. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:

*Family.*—Rosaceae.
*Species.*—*Prunus fruiticosa* x *Prunus cerasus.*
*Variety.*—'Big Red'.

Parentage:

*Female parent.*—*Prunus fruiticosa* 'Egbert Center' (unpatented).
*Male parent.*—*Prunus cerasus* 'Kelleris 14' (unpatented).

Tree:
*Type*.—Softwood cuttings onto root stock of 'Carmine Jewel'.
*Height*.—1.5 m.
*Width*.—1.5 m.
*Vigor*.—Medium.
*Density of foliage*.—Medium.
*Form*.—Upright and spreading bush.
*Disease response*.—Slight resistance to Cherry Leaf Spot (*Blumeriella jaapii*).
*Insect response*.—Strong resistance to Black Cherry Aphids (*Myzus cerasi*), strong resistance to Peach Tree Borer (*Synanthedon exitiosa*).

Trunk:
*Diameter*.—5.2 cm.
*Lenticel length*.—3.0 mm to 7.0 mm.
*Lenticel width*.—1.0 mm.
*Lenticel shape*.—Very narrow elliptic.
*Lenticel color*.—RHS 163A, Beige.
*Lenticel number*.—7 to 11 per 5 square centimeters.
*Bark texture and appearance*.—Mostly smooth with medium roughness around the lenticels and flaking with age.
*Bark color*.—RHS 166A.

Branches, 1-year-old wood:
*Vertical top growth length*.—28.0 cm.
*Horizontal growth length*.—19.0 cm.
*Diameter, vertical growth*.—4.0 mm to 5.0 mm.
*Diameter, horizontal growth*.—3.0 mm.
*Internode length*.—2.0 cm to 2.5 cm.
*Number of lenticels per branch*.—12.
*Lenticel size*.—1.0 mm length and 1.0 mm width.
*Lenticel shape*.—Round.
*Lenticel color*.—RHS 164B fading to RHS 164C on the edges.
*Texture*.—Slightly rough from the lenticels.
*Branch color*.—RHS 197B.

Branches, 2-year-old wood:
*Length*.—42.0 cm.
*Diameter*.—6.0 mm to 8.0 mm.
*Internode length*.—2.5 cm to 3.5 cm.
*Number of lenticels per branch*.—20.
*Lenticel size*.—2.0 mm length and 0.5 mm width.
*Lenticel shape*.—Elliptic.
*Lenticel color*.—RHS 164B.
*Texture*.—Slightly rough from the lenticels.
*Branch color*.—RHS 187B.

Vegetative buds:
*Shape*.—Triangular.
*Length*.—3.0 mm.
*Width*.—3.0 mm.
*Color*.—RHS 176A.

Mature leaves:
*Length*.—8.2 cm to 10.1 cm.
*Width*.—3.5 cm to 5.5 cm.
*Shape*.—Elliptic.
*Apex*.—Acuminate.
*Base*.—Rounded.
*Margin*.—Serrulate.
*Surface texture* (*both upper and lower surfaces*).—Glabrous with a few short hairs.
*Color*.—Upper surface: RHS 139A. Lower surface: RHS 137B.
*Petiole*.—Color: RHS 147C. Length: 12 mm to 15 mm. Diameter: 2 mm.
*Glands*.—Number: 2. Length: 0.5 mm. Width: 1.0 mm. Shape: Truncate. Location: On the base of the leaf blade and petiole. Color: Concentric rings; outer ring is RHS 59A and inner ring is RHS 145C; sometimes has black centers, RHS 202A.
*Stipule*.—Absent.

Flower:
*Diameter*.—4.2 mm.
*Bloom period*.—April 25 to May 5.
*Bud*.—Shape: Subglobose. Length: 9.0 mm. Diameter: 4.0 mm. Texture: Smooth. Color: RHS 181C.
*Petals*.—Number per flower: 5. Length: 1.8 cm to 2.0 cm. Width: 1.3 cm to 1.5 cm. Shape: Obovate. Apex: Slightly rounded. Base: Cuneate. Texture (both upper and lower surfaces): Smooth. Margin: Entire. Margin waviness: Slight. Color (both upper and lower surfaces): RHS N99D.
*Peduncle*.—Length: 3.0 cm. Width: 1.0 mm. Color: RHS 144A. Texture: Smooth.
*Sepals*.—Number per flower: 5. Apex: Acute. Base: Broad. Margin: Dentate. Shape: Narrowly triangular and towards deltoid. Texture (both upper and lower surfaces): Glaucous with slight furrows. Color: Upper surface: RHS 137B. Lower surface: RHS 137C. Length: 6.0 mm. Width: 3.0 mm. Shape: Narrowly ovate. Color (both upper and lower surfaces): Center is RHS 149D and deepens to RHS 144A towards the tip.

Reproductive organs:
*Filament color*.—RHS N99D.
*Filament length*.—8.0 mm.
*Filament width*.—0.25 mm.
*Anther shape*.—Cardioid.
*Anther length*.—1.0 mm.
*Anther width*.—0.9 mm.
*Anther color*.—RHS 15B.
*Pollen amount*.—Moderate.
*Pollen color*.—RHS 16B.
*Self-compatibility of flowers*.—Present.
*Stamen number per flower*.—1.
*Pistil length*.—11.0 mm.
*Style length*.—7.0 mm.
*Style color*.—RHS 143A.
*Stigma shape*.—Lobed.
*Ovary color*.—RHS 143B.

Fruit:
*Use*.—Fresh, cooking, preserves.
*Keeping quality*.—Good.
*Flavor*.—Mildly tart.
*Juice color*.—RHS 58D.
*Individual fruit weight*.—4.6 g to 6.1 g.
*Shape of fruit*.—Elongated flat heart.
*Fruit length*.—23.0 mm.
*Fruit diameter*.—13.0 mm.
*Skin thickness*.—Thin.
*Skin texture*.—Smooth.
*Tenacity to crack*.—Moderate.
*Skin color*.—RHS 53A.
*Flesh texture*.—Soft, juicy, and melting.
*Aroma*.—Faint.
*Fruit flesh color*.—RHS 45A to RHS 45C; flesh around the pit is RHS 28C.
*Seed/pit shape*.—Ovate.

*Seed/pit length.*—13.0 mm.

*Seed/pit width.*—9.0 mm.

*Seed/pit color.*—RHS 167C.

*Harvest date and quantity per tree per growing season.*—As observed in Tipp City, Ohio, harvest is from about June 29 to July 11 and quantity of fruit per tree obtained is 3.5 kg.

COMPARISON WITH PARENTAL AND COMMERCIAL LINES

Table 1 shows a comparison of differences between 'Big Red' and both parental lines.

TABLE 1

| Comparison with Parental Lines | | | |
|---|---|---|---|
| Characteristic | 'Big Red' | Female parent, 'Egbert Center' | Male parent, 'Kelleris 14' |
| Fruit description | Bright red, slightly sweet, juicy, elongated heart-shaped | Dark red, sour tasting and watery | Round, dark red, sweet tart in flavor |

TABLE 1-continued

| Comparison with Parental Lines | | | |
|---|---|---|---|
| Characteristic | 'Big Red' | Female parent, 'Egbert Center' | Male parent, 'Kelleris 14' |
| Growth habit | Spreading bush | Upright with central leader | Small |

Table 2 shows a comparison of the differences between 'Big Red' and the commercial cherry variety 'Montmorency' (unpatented).

TABLE 2

| Comparison with Commercial Line | | |
|---|---|---|
| Characteristic | 'Big Red' | 'Montmorency' |
| Height | 1.5 m | 4.5 m to 5.4 m |

We claim:

1. A new and distinct variety of cherry tree designated 'Big Red' as illustrated and described herein.

* * * * *